(12) United States Patent
Brandt

(10) Patent No.: US 9,636,648 B2
(45) Date of Patent: May 2, 2017

(54) SYSTEM AND METHOD FOR COMPENSATING BINARY INLET BUFFERS DURING INLINE BUFFER DILUATION

(71) Applicant: Asahi Kasei Bioprocess, Inc., Glenview, IL (US)

(72) Inventor: Michael Brandt, Lincolnshire, IL (US)

(73) Assignee: ASAHI KASEI BIOPROCESS, INC., Glenview, IL (US)

( * ) Notice: Subject to any disclaimer, the term of this patent is extended or adjusted under 35 U.S.C. 154(b) by 0 days.

(21) Appl. No.: 15/048,445

(22) Filed: Feb. 19, 2016

(65) Prior Publication Data

US 2016/0243512 A1    Aug. 25, 2016

Related U.S. Application Data

(60) Provisional application No. 62/118,355, filed on Feb. 19, 2015.

(51) Int. Cl.

| | |
|---|---|
| *B01F 15/00* | (2006.01) |
| *B01F 15/02* | (2006.01) |
| *G01F 1/00* | (2006.01) |
| *G01N 21/41* | (2006.01) |
| *G01N 27/10* | (2006.01) |
| *G01N 27/416* | (2006.01) |
| *G05D 11/13* | (2006.01) |

(52) U.S. Cl.
CPC .... *B01F 15/00331* (2013.01); *B01F 15/0022* (2013.01); *B01F 15/00136* (2013.01); *B01F 15/00207* (2013.01); *B01F 15/00227* (2013.01); *B01F 15/0243* (2013.01); *G01F 1/00* (2013.01); *G01N 21/4133* (2013.01); *G01N 27/10* (2013.01); *G01N 27/4167* (2013.01); *G05D 11/138* (2013.01)

(58) Field of Classification Search
CPC ............... B01J 14/00; B01F 14/00331; B01F 15/00136; B01F 15/00207; B01F 15/0022; B01F 15/0243; G01N 27/10; G01N 27/4167; G01F 1/00; G05D 11/138
See application file for complete search history.

(56) References Cited

U.S. PATENT DOCUMENTS

| | | |
|---|---|---|
| 2003/0031086 A1 | 2/2003 | Shikami et al. |
| 2005/0273203 A1 | 12/2005 | Bellafiore et al. |
| 2012/0217192 A1 | 8/2012 | Blank et al. |
| 2013/0081703 A1 | 4/2013 | Andrei et al. |
| 2014/0340980 A1 | 11/2014 | Brandt |

OTHER PUBLICATIONS

International Search Report and Written Opinion from PCT Application No. PCT/US2016/018711 mailed May 2, 2016.

*Primary Examiner* — Brian R Gordon
(74) *Attorney, Agent, or Firm* — DLA Piper LLP (US); Jennifer Lacroix

(57) ABSTRACT

Liquid blending systems and methods of blending liquids are provided. In particular, systems and methods for compensating binary inlet buffers during inline buffer dilution are provided. The systems and methods can provide blends of diluent, a first buffer concentrate containing a majority of a tempering component, and a second buffer concentrate containing a minority of a tempering component. The flow of the first buffer concentrate can be adjusted based upon the total amount of the tempering component being added to the blend through the first and second buffer concentrates.

6 Claims, 3 Drawing Sheets

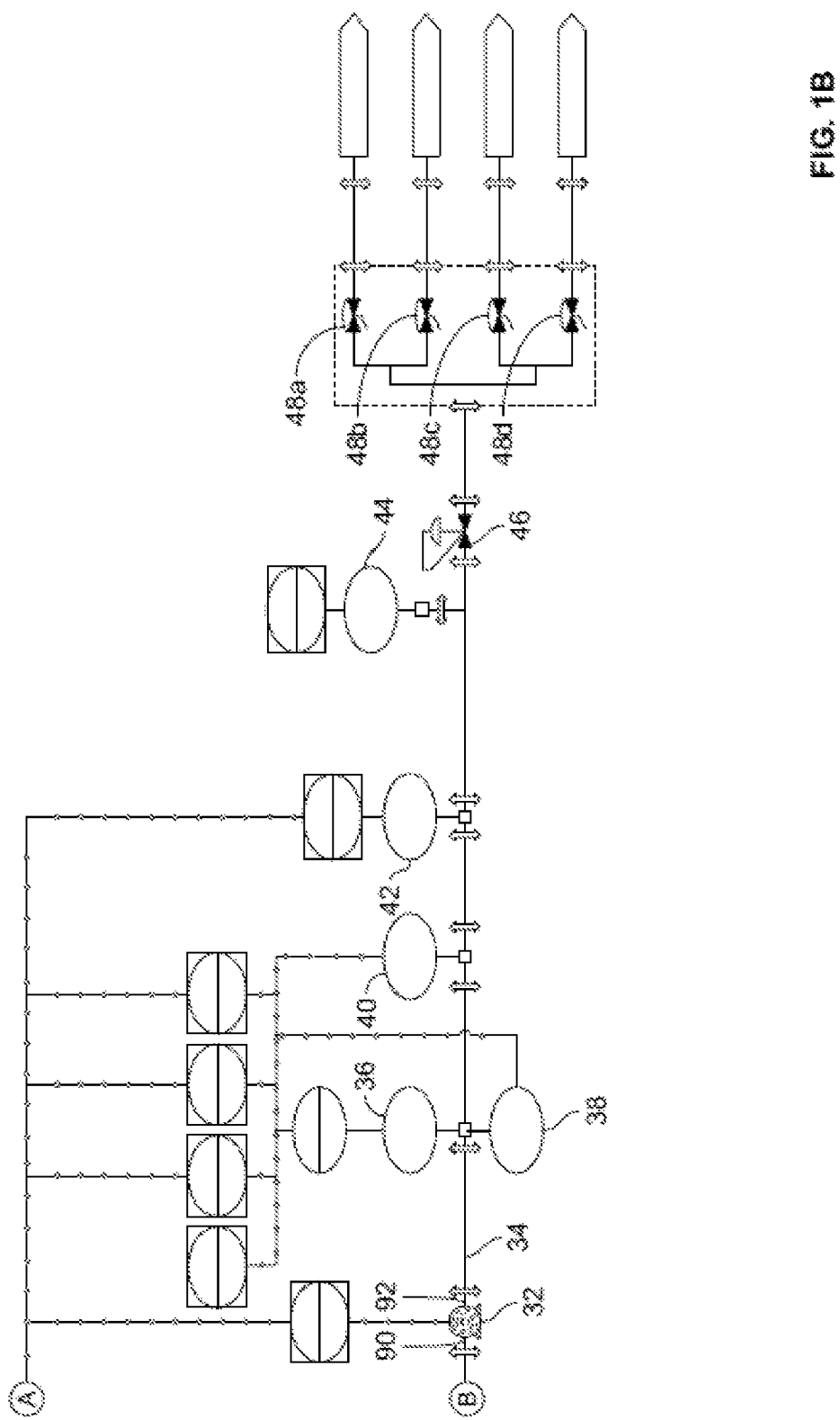

SYSTEM AND METHOD FOR COMPENSATING BINARY INLET BUFFERS DURING INLINE BUFFER DILUATION

CLAIM OF PRIORITY

This application claims priority to U.S. Provisional Application No. 62/118,355, filed on Feb. 19, 2015, the content of which is incorporated herein by reference.

FIELD OF THE INVENTION

The present invention relates generally to liquid blending systems and methods and, in particular, to a system and method for compensating binary inlet buffers during inline buffer dilution.

BACKGROUND

The combining of two or more liquids together to a desired concentration and/or other characteristics or properties, such as pH, conductivity, optical density, refractive index, etc., of the constituent liquids is fundamental to many industrial processes and commercial products. This combining of liquids may be referred to as blending and is common in many industrial segments. In addition, blending systems find use in the field of liquid chromatography where blended liquids are provided to chromatography columns to permit the separation of mixtures for analysis or for purification purposes.

On site blending systems provide many advantages over purchasing pre-mixed chemicals. By using a blending system, a single quantity of feedstock concentrate can be used to produce many times its volume in diluted solution, depending on the desired concentration of the dilution. Thus, a single feedstock concentrate, used to produce the equivalent of many feedstocks of dilute liquid via, a blending system can greatly reduce facility costs associated with fabrication of large tanks, floor space required, validation and quality control costs to confirm makeup, as well as spoilage and disposal costs of non-compliant out of date or unused blended solutions. Freight costs associated with chemical delivery can also be reduced. In addition, onsite dilution and blending increases the variety of chemical concentrations and mixtures that are immediately available, without requiring a corresponding increase in the number of feedstocks and chemicals that must be purchased, thereby reducing facility and operating costs and providing the logistical and administrative advantage of reduced inventory.

High accuracy in terms of concentration for blending systems providing liquids to liquid chromatography systems is desirable. In addition, quality control concerns favor increased blending accuracy for liquids that are provided to industrial processes and that are used to create commercial products. Indeed, Six Sigma quality control principles dictate that lower variability in an industrial process results in a greater percentage of higher quality products being produced by the industrial process.

It is well known, however, that there will be variations in concentration within a feedstock. For example, it is common for different portions of a large feedstock tank filled with a solution to have different proportionate mixtures of the constituent liquids. Gradients exist in large feedstocks in terms of both concentration and temperature. As a result, liquid provided from the feedstock will vary in terms of concentration, which poses challenges for accurate analysis, quality control analysis, and uniform delivery to a process. Feedstock solvents, commercially supplied, have variations in actual concentration from batch to batch, as well as innate impurities, which prevents 100% pure concentrations from being available in bulk supply. In response, systems and methods for accurately blending liquids from such feedstocks, such as the Inline Buffer Dilution systems and methods using Process Analytical Technology (PAT) in commonly assigned U.S. Pat. Nos. 7,072,742; 7,515,994 and 8,271,139, all to Bellafiore et al., have been developed.

When a blend is simply a dilution of a buffer concentrate with water or other diluent, it is known as a binary blend. When a blend is accomplished by way of dilution of multiple buffer concentrates with water or other diluent, it is known as a ternary blend when it has three components, a quaternary blend when it has four components, and so on with names indicating the number of components being blended. A common example of ternary blending is when two concentrate solutions are simultaneously diluted with water or other diluent to form a specific ternary blend. The inlet concentrates may be of any form, such as salts or conjugate forms of a buffer, or a form of a buffer (concentrate) that is to be tempered with a form of an acid or base.

A less common example of ternary blending is the incorporation of refractive index (RI) inline process measurement with conductivity inline process measurement. Temperature control can be incorporated in such examples (and in other cases) in order to reduce the matrix effect of temperature to two measures, two variables.

Factors such as target conductivity, pH, and/or other component concentration of the blend can be significant with respect to the process application to which the blend is applied. The processes these blends are used for are greatly diversified but in general, may be used to feed a final product manufacturing process, biological growth, separation or purification process, etc.

As described in the commonly assigned U.S. Pat. Nos. 7,072,742; 7,515,994 and 8,271,139, the special purpose of the Inline Buffer Dilution equipment using PAT is the ability to consistently obtain the target conductivity and/or pH and/or other component concentration of the blend independent of upstream variability which may occur in the inlet concentration of the buffer concentrates or diluent composition. Due to the limitations of the analytical technologies available for PAT feedback/control, however, it is sometimes necessary to construct blends using flow control and flow meters as the feedback (to the programmable logic controller) to proportion two or more components in the blend. A drawback of the Inline Buffer Dilution equipment using flow control is the flow meter's inability to compensate for the potential/inherent variability of the inlet buffer (or diluent) concentration. Specifically, flow control fundamentally cannot be used to target desired pH within commonly acceptable precision. Thus, in a ternary blend where flow control is used to accomplish the target blend between the first concentrate buffer and the diluent, and pH control is desired, pH feedback/control of the second concentrate buffer must be used to accomplish pH tempering to a high degree of precision.

In some circumstances in the above scenario, the second inlet buffer concentrate being used for pH tempering (or tempering of conductivity or other property) must be a binary mixture containing as its minority component the compound which is the majority component of the first buffer concentrate. As a result, when the diluent and the first buffer concentrate must be proportioned by flow control, the proportion between the diluent and the first concentrate being controlled by flow would, by the addition of the (for example) pH tempering solution, with its minority component being the same as the first buffer concentrate, be unaccounted for in volume added to the final solution and spoil the proportion intended between the first buffer concentrate and the diluent. A need therefore exists for a system and method that addresses these issues.

BRIEF DESCRIPTION OF THE DRAWINGS

FIGS. 1A and 1B together form a schematic illustrating one embodiment of a system of the present technology.

DETAILED DESCRIPTION OF EMBODIMENTS

Systems and methods of the present technology can be used for compensating binary inlet buffers during inline buffer dilution.

In accordance with some embodiments of the present technology, as explained in greater detail below, a flow meter monitors the flow of the pH tempering solution, but the system does not have it feedback to the control of the pH tempering. The feedback to control the pH tempering solution (binary mixture) is from the pH meter or sensor in a feedback loop. The flow meter monitoring the flow of the pH tempering solution is used in conjunction with the known concentration of the minority component in a calculation to compensate the flow quantity of the first buffer concentrate to produce the desired flow-based final blend with feedback-based pH tempering.

While examples of the present technology are described below primarily in terms of ternary blending with feedstock and a binary pH tempering solution, the present technology can be used in other applications. For example, the present technology may also be used with blending a feedstock with a conductivity binary tempering solution, a refractive index binary tempering solution, or a binary solution for tempering another property in place of the these example tempering solutions. In addition, the system and method of the present technology may be used with a greater number of components than ternary blending (e.g., quaternary blending, etc.), such as blending two or more feedstocks with at least one tempering solution.

Figure 1A:
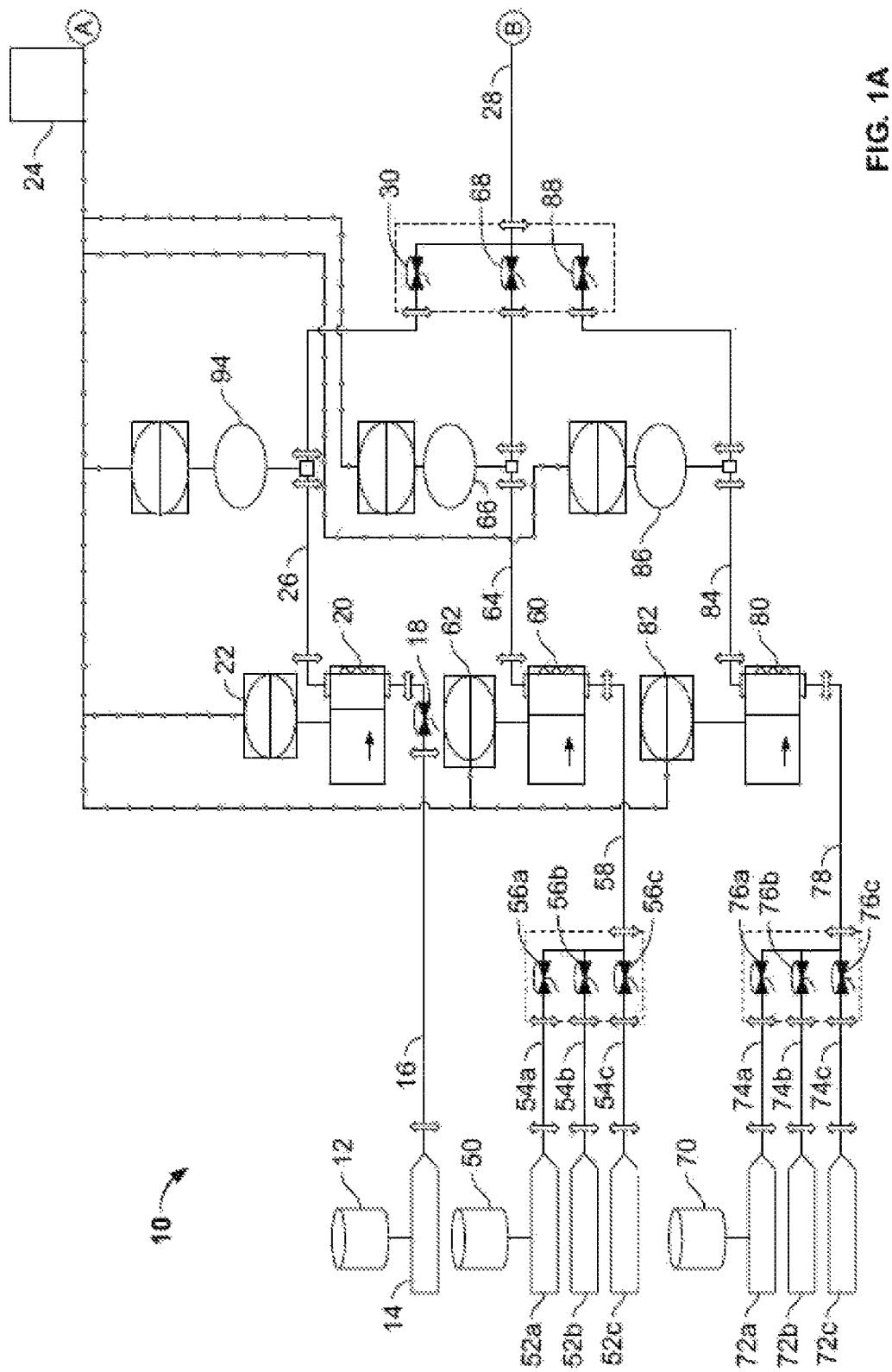

One embodiment of a system of the present technology is indicated in general at 10 in FIGS. 1A and 1B. As shown, a diluent 12, such as, for example, compendial water, is connected to the system 10 at a first port or inlet 14. The a first port 14 is adapted to receive the diluent 12, and the diluent 12 then travels through line 16 to inlet valve 18, which can be opened to allow flow into a first pump 20. Pump 20 is driven by first speed control 22, which is controlled by a programmable logic controller 24. The first pump 20 can have an inlet in communication with the first port 14 and an outlet in communication with the inlet 90 of the mixer 32. For example, as illustrated, from pump 20, the diluent can be driven through line 26, and into line 28 when valve 30 is opened. The diluent can flow through line 28 and into mixer 32 through the inlet 90 of the mixer 32.

As shown in FIG. 1B, the product stream from the mixer flows out of the mixer 32 through outlet 92 of the mixer, and then through product line 34, which can include at least one property sensor for measuring a desired property of the product stream. The at least one property sensor is in communication with the outlet 92 of the mixer. In the illustrate example, the property sensors can include: conductivity sensor 36, pH sensor 38, refractive index sensor 40, a first flow meter 42 and a pressure transmitter 44. The first flow meter 42 can be in communication with the outlet 92 of the mixer. At the pressure transmitter 44, the product stream in product line 34 interacts with a backpressure regulator 46, and then flows into a series of outlet valves 48a-d, which can be opened as appropriate for directing the blend.

As also shown in FIGS. 1A and 1B, a first buffer concentrate 50 having a majority component is connected to the system 10 by at least one second port or inlet, which as illustrated includes inlets 52a, 52b, and 52c. The second port 52a-c is adapted to receive the first buffer concentrate, and the first buffer concentrate 50 travels from the at least one second port 52a-c through at least one line 54a, 54b, 54c (respectively) to an inlet valve 56a, 56b, 56c (respectively) which can be opened to allow flow through line 58 into a second pump 60. The first buffer concentrate 50 can be driven through the pump 60 by a second speed control 62 that is controlled by the programmable logic controller 24. The second pump 60 can have an inlet in communication with the second port 52a-c and an outlet in communication with the inlet of the second flow meter 66. For example, as illustrated, after passing through the pump 60, the first buffer concentrate 50 can pass through line 64 to a second flow meter 66, and then to valve 68 which can be opened to allow flow through line 28 and into mixer 32 through the inlet 90 of the mixer 32.

As further shown in FIGS. 1A and 1B, a second buffer concentrate 70, which is a binary mixture having a minority component that is the same as the majority component of first buffer concentrate 50, is connected to system 10 by at least one third port or inlet, which as illustrated includes inlets 72a, 72b, and 72c. The second buffer concentrate 70 travels from the at least one third inlet through at least one line 74a, 74b, 74c (respectively) to an inlet valve 76a, 76b, 76c (respectively) which can be opened to allow flow through line 78 into a third pump 80. The second buffer concentrate 70 can be driven through the pump 80 by a third speed control 82 that is controlled by the programmable logic controller 24. The third pump 80 can have an inlet in communication with the third port and an outlet in communication with the inlet of the third flow meter 86. For example, as illustrated, after passing through the pump 80, the second buffer concentrate 70 can pass through line 84 to a third flow meter 86, and then to valve 88 which can be opened to allow flow through line 28 and into mixer 32 through the inlet 90 of the mixer 32. The third flow meter 86 can have an inlet in communication with the third port 72a-c and an outlet in communication with the inlet 90 of the mixer 32.

In some embodiments, as shown in FIG. 1A, a fourth flow meter 94 can be placed such that it has an inlet in communication with the first port 14 and an outlet in communication with the inlet 90 of the mixer 32. As illustrated, after passing through the pump 20, the diluent 12 can pass through line 26 to the third flow meter 94, and then to valve 30 which can be opened to allow flow through line 28 and into mixer 32 through the inlet 90 of the mixer 32.

A programmable logic controller 24 can be in communication with at least each of the flow meters, each of the speed controls for the pumps, and each property sensor. The programmable logic controller 24 can be programmed, through computer readable instructions stored on a non-transient medium such as a memory, to operate the system. For example, the programmable logic controller 24 can perform the following functions:

i) adjust the first pump based on the first and/or fourth flow meter;

ii) adjust the third pump based on the sensor; and iii) adjust the second pump based on the second flow meter and the third flow meter.

The systems and system operation methods of the present technology can achieve a continuous blend at a target total flowrate, at a target flow dilution between the diluent and the first buffer concentrate by flow feedback/control, with a target pH adjustment in the final product by pH feedback/control, with the pH adjustment solution being a binary mixture containing as its minority component the same majority component as the first buffer concentrate. As noted previously, while pH is used as a example of a target property, other properties including, but not limited to, conductivity and refractive index may be used as the target property.

Figure 2:
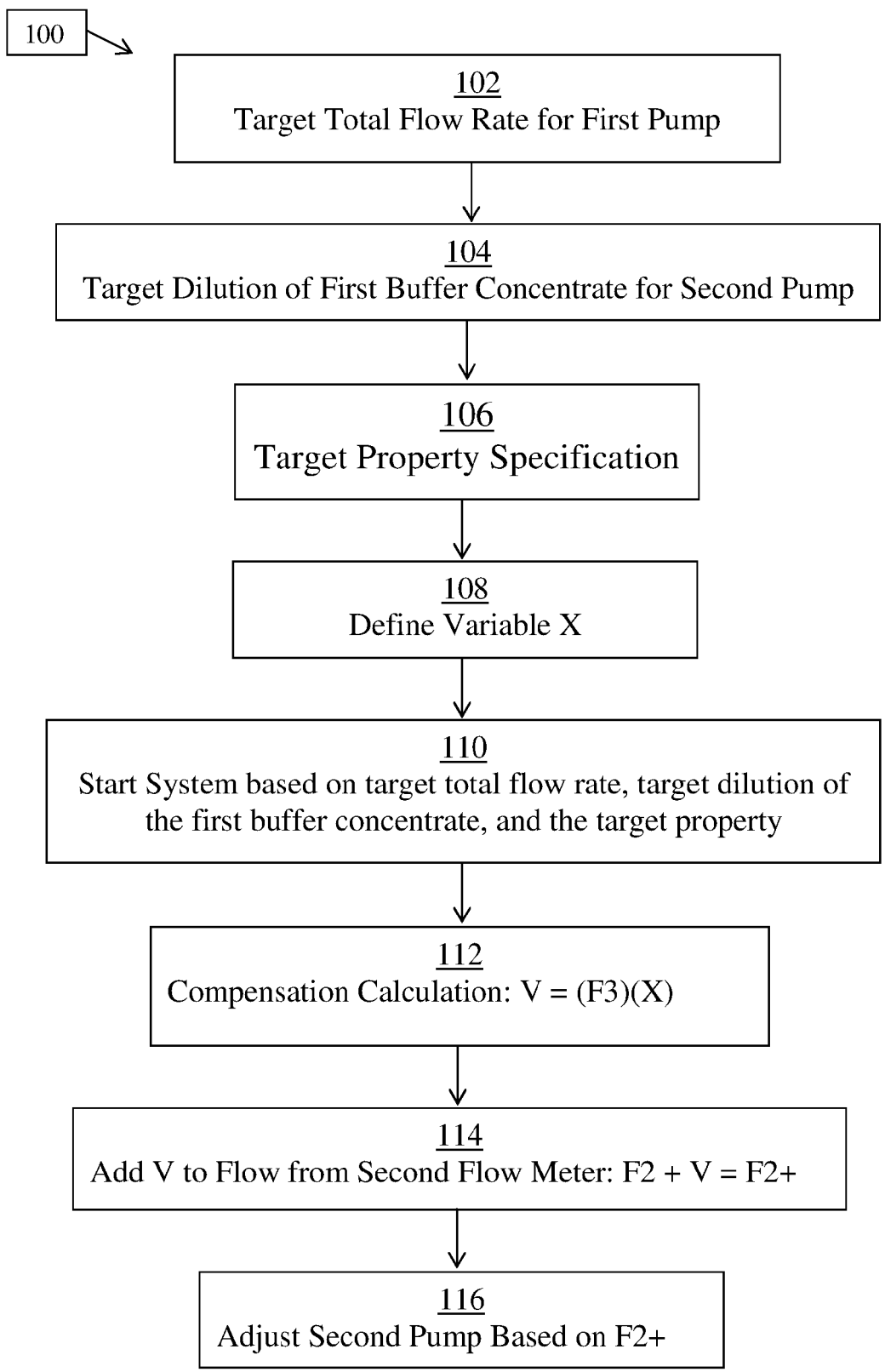
FIG. 2 is a flow chart showing a method of operating the system of FIG. 1.

One method of operating a system of the present technology is shown in FIG. 2, with reference to system 10 as shown in FIGS. 1A and 1B. The method can be carried out by programmable logic controller 24, which controls and receives feedback from the components of the system 10. It is to be understood that the steps illustrated in FIG. 2 do not necessarily have to be performed in the order illustrated.

The system operation method is indicated generally at 100. As indicated at step 102, the programmable logic controller 24 receives a target total flowrate for the first pump 20, which can be entered as the set point into a proportional-integral-derivative (PID) feedback loop controller of programmable logic controller 24, and the PID loop for the first pump 20 can be set to flow feedback/control.

As indicated at step 104, the programmable logic controller 24 receives a target dilution of the first buffer concentrate, which can be entered as the set point in a PID feedback loop controller of programmable logic controller 24 for second pump 60, and the PID loop for second pump 60 can be set to flow feedback/control.

As indicated at step 106, the programmable logic controller 24 receives the specifications for the desired target property of the product stream, which can be entered as the set point in a PID feedback loop controller of programmable logic controller 24 for the third pump 80, and the loop for the third pump 80 can be set to feedback/control for the target property. As discussed above, the target property can be pH, or alternatively other properties such as conductivity and refractive index.

In addition, as indicated at step 108, the programmable logic controller 24 receives a concentration of the minority component of the second buffer concentrate 70, which can be entered as a variable X defined as the ratio given by the weight of the minority component in second buffer concentrate 70 over total weight of second buffer concentrate 70.

At step 110, the system 10 can be started based on the target total flow rate, target dilution of the first buffer concentrate, and the target property. The programmable logic controller 24 can drive first pump 20 and the second pump 60 to their respective speeds to accomplish their respective set points based on flow feedback control from first flow meter 42 and second flow meter 66, respectively. The second flow meter 66 has an inlet in communication with the second port 52a-c and an outlet in communication with the inlet 90 of the mixer 32. The product pH sensor 38 in the feedback/control loop with the third pump 80, can drive the third pump 80 to accomplish the pH set point. Alternatively, the conductivity sensor 36 and/or the refractive index sensor 40 in the feedback/control loop with the third pump 80 can drive the third pump 80 to accomplish the conductivity or refractive index set point. In alternative embodiments, other product property sensors may be used.

As indicated previously, without consideration of the concentration of the minority component in the second buffer, binary solution (second buffer concentrate 70 of FIG. 1A), addition of the pH tempering solution (to adjust pH) would add an unknown amount of the minority component of the second buffer, binary solution (which contains a small portion of the majority component of the first buffer concentrate 50 of FIG. 1A) to the final product exiting the system through valves 48a-d and spoil the intended flow based dilution between the first buffer concentrate 50 and the diluent 12. In other words, the minority component in the second buffer, binary solution (second buffer concentrate 70) would generally act as an undesired additional amount of first buffer concentrate 50.

As indicated at step 112, the programmable logic controller 24 can perform a compensation calculation to compensate for the additional amount of the minority component of second buffer concentrate 70 added to the final product as the pH is accurately tempered to the set point by the pH feedback/control loop with the third pump 80. In the compensation calculation, set forth below, flow from third flow meter 86, referred to in the equation below as F3, can be monitored by the programmable logic controller 24 and multiplied by X to give V, which is the additional amount of the component added per unit time (V):

$$F3 \times X = V$$

As indicated at step 114, the programmable logic controller 24 can determine the actual amount of the tempering component being added by adding V to the flow measured from the second flow meter 66, defined as F2 in the equation below, to obtain actual tempering component concentrate flow (F2+):

$$F2 + V = F2+$$

As indicated at step 116, by using F2+ as the measured flow of the tempering component concentrate in the feedback/control loop, the programmable logic controller 24 can adjust the speed of the second pump 60 by controlling the second speed control 62. The adjustment of the speed of the second pump can be based on the value of F2+ to establish the target flow based dilution for the final solution independent of the pH which is being adjusted by the pH feedback/control loop with the third pump 80 (as previously mentioned).

The programmable logic controller 24 can determine the flow setpoint of the first pump 20 based on feedback received from fourth flow meter 94, the flow F2 measured from the second flow meter 66, and the flow F3 flow measured from third flow meter 86.

Example 1

It is desired to make a phosphate buffered saline solution at physiological pH and seawater concentration. Buffer 1 contains the sodium salt concentrate. When Buffer 1 is diluted to the desired saline (sodium salt) concentration, the pH in the final solution must be tempered to achieve physiological (pH) conditions. Buffer 2 is the tempering solution (phosphate buffer) that for shelf life purposes has a minority component of sodium salt 10%.

$X$=minority component weight of Buffer 2/total weight of Buffer 2=0.1

The above amount is entered for X into the programmable logic controller 24.

In addition, the following set points are entered into the programmable logic controller 24:

Total flowrate desired is 5 liter a minute;
Buffer 1 is 5 times concentrate saline.

When the flow based dilution starts, first flow meter 42 or the fourth flow meter 94 can be used to control the first pump 20 to the set point 4 times the flowrate F2 of the second flow meter 66 as established by the second pump 60:

$F2 = 1$ liter per minute.

The third pump 80 will begin to adjust the pH by pH feedback/control adding tempering solution 70 (Buffer 2) which is counted as water by the first flow meter 42 by virtue of its position in the flow path. Thus the flow proportion between first and second flow meters 42 and 66 is automatically maintained, but Buffer 2, being added by third pump 80, has a minority component of saline which is not accounted for by first flow meter 42—just the volume flow is accounted for. If the saline component (10% minority component of sodium salt) in Buffer 2 is not accounted for, it would corrupt the intended proportion between the first flow meter 42 and the second flow meter 66, that is, 5 times dilution.

To account for the sodium salt minority component in Buffer 2, the third flow meter 86 is interrogated by the programmable logic controller 24, which then adds the volume of the minority component to the flow recorded by the second flow meter 66. For example: flow F3 may be 1/10 of flow F2 to obtain target pH:

$F3 = 0.1 \times 1 = 0.1$ liter per minute

The additional Buffer 1 component added per unit time V therefore is:

$V = F3 \times X = 0.1 \times 0.1 = 0.01$

The contribution of saline added to F2 therefore results in:

$F2+ = 1 + 0.01 = 1.01$ liter per minute.

The programmable logic controller 24 would then back off/lower the speed of the second pump 60 so that F2+ is controlled at 1 liter per minute in order to maintain the desired ratio between the first and second flow meters 42 and 66 and the final concentration of saline desired is obtained while the pH desired is maintained.

While the preferred embodiments of the invention have been shown and described, it will be apparent to those skilled in the art that changes and modifications may be made therein without departing from the spirit of the invention.

What is claimed is:

1. A system for compensating binary inlet buffers during inline buffer dilution comprising:
   a. a diluent received through a first port;
   b. a first buffer concentrate received through a second port, the first buffer concentrate having a majority component;
   c. a second buffer concentrate received through a third port, the second buffer concentrate being a binary mixture having a minority component that is the same as the majority component of the first buffer concentrate;
   d. a mixer having an inlet and an outlet;
   e. a first flow meter in communication with the outlet of the mixer;
   f. a second flow meter having an inlet in communication with the second port and an outlet in communication with the inlet of the mixer;
   g. a third flow meter having an inlet in communication with the third port and an outlet in communication with the inlet of the mixer;
   h. a property sensor in communication with the outlet of the mixer that measures a property of a product stream from the mixer;
   i. a first pump having an inlet in communication with the first port and an outlet in communication with the inlet of the mixer;
   j. a second pump having an inlet in communication with the second port and an outlet in communication with the inlet of the second flow meter;
   k. a third pump having an inlet in communication with the third port and an outlet in communication with the inlet of the third flow meter;
   l. a controller in communication with the first, second and third flow meters, the first second and third pumps and the property sensor, said controller programmed to:
      i) adjust the first pump based on feedback from the first flow meter;
      ii) adjust the third pump based on feedback from the property sensor;
      iii) adjust the second pump based on feedback from the second flow meter and the third flow meter.

2. The system of claim 1, further comprising a fourth flow meter having an inlet in communication with the first port and an outlet in communication with the inlet of the mixer.

3. The system of claim 1 wherein the property sensor is a pH sensor.

4. The system of claim 1 wherein the controller adjusts:
   i) the first pump based on a target total flow rate and flow feedback from the first flow meter;
   ii) the third pump based on a target property of the product stream and feedback from the property sensor;
   iii) the second pump based on a target dilution of the first buffer concentrate by the diluent, flow feedback from the second flow meter (F2), the third flow meter (F3), and a concentration of the minority component in the second buffer concentrate (X), wherein:
      an amount (V) of the minority component of the second buffer concentrate added per unit of time is calculated as $F3 \times X = V$;
      an total amount (F2+) of the component from the first buffer concentrate and the second buffer concentrate is calculated as $F2+V=F2+$; and
      the controller adjusts a speed of the second pump based on F2+.

5. The system of claim 2 wherein the property sensor is a pH sensor.

6. The system of claim 2, wherein the controller is programmed to:
   i) adjust the first pump based on feedback from the first flow meter and the fourth flow meter;
   ii) adjust the third pump based on feedback from the property sensor;
   iii) adjust the second pump based on feedback from the second flow meter and the third flow meter.

* * * * *

UNITED STATES PATENT AND TRADEMARK OFFICE
CERTIFICATE OF CORRECTION

PATENT NO. : 9,636,648 B2
APPLICATION NO. : 15/048445
DATED : May 2, 2017
INVENTOR(S) : Michael Brandt It is certified that error appears in the above-identified patent and that said Letters Patent is hereby corrected as shown below:

On the Title Page

Item [54], Title, replace "SYSTEM AND METHOD FOR COMPENSATING BINARY INLET BUFFERS DURING INLINE BUFFER DILUATION" with -- SYSTEM AND METHOD FOR COMPENSATING BINARY INLET BUFFERS DURING INLINE BUFFER DILUTION --

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*